(12) United States Patent
Wagner et al.

(10) Patent No.: US 8,785,587 B2
(45) Date of Patent: Jul. 22, 2014

(54) POLYUREA- AND/OR POLYURETHANE-POLYORGANOSILOXANE COMPOUNDS

(75) Inventors: Roland Wagner, Bonn (DE); Karl-Heinz Sockel, Leverkusen (DE); Anita Witossek, Langenfeld (DE); Walter Simon, Leverkusen (DE)

(73) Assignee: Momentive Performance Materials GmbH, Leverkusen (DE)

( * ) Notice: Subject to any disclaimer, the term of this patent is extended or adjusted under 35 U.S.C. 154(b) by 501 days.

(21) Appl. No.: 12/673,009

(22) PCT Filed: Aug. 14, 2008

(86) PCT No.: PCT/EP2008/060681
§ 371 (c)(1),
(2), (4) Date: Feb. 11, 2010

(87) PCT Pub. No.: WO2009/021989
PCT Pub. Date: Feb. 19, 2009

(65) Prior Publication Data
US 2011/0182844 A1 Jul. 28, 2011

(30) Foreign Application Priority Data
Aug. 14, 2007 (DE) .......... 10 2007 038 447

(51) Int. Cl.
*C08G 77/28* (2006.01)

(52) U.S. Cl.
USPC ........................ 528/28; 424/70.122

(58) Field of Classification Search
USPC ........................ 528/28; 424/70.122
See application file for complete search history.

(56) References Cited

U.S. PATENT DOCUMENTS

| 5,104,930 A * | 4/1992 | Rinde et al. ............ 524/871 |
| 5,120,813 A | 6/1992 | Ward, Jr. |
| 5,290,615 A * | 3/1994 | Tushaus et al. .......... 428/41.4 |
| 7,560,166 B2 * | 7/2009 | Moore et al. ........... 428/447 |
| 2004/0087752 A1 | 5/2004 | Schindler et al. |
| 2008/0027201 A1 * | 1/2008 | Yilgor et al. ............ 528/28 |

FOREIGN PATENT DOCUMENTS

| DE | 1570576 | 12/1969 |
| GB | 1128642 | 9/1968 |
| WO | 2004/104070 | 12/2004 |
| WO | 2008/113831 | 9/2008 |

OTHER PUBLICATIONS

Preliminary Report on Patentability for corresponding PCT/EP2008/060681 mailed Mar. 11, 2010, eight pages.
International Search Report for corresponding PCT/EP2008/060681 mailed Dec. 29, 2008, three pages.

* cited by examiner

*Primary Examiner* — Margaret Moore
(74) *Attorney, Agent, or Firm* — Rankin, Hill & Clark LLP

(57) ABSTRACT

The invention relates to novel polyurea- and/or polyurethane polyorganosiloxane compounds, processes for the preparation thereof, and their use and novel reactive 1- or 2-component systems and cured compositions therefrom. The compounds preferably contain repeating units of the formula (2):

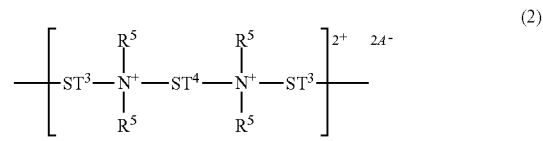

in the polyurea- and/or polyurethane polyorganosiloxane backbone. The polyurea- and/or polyurethane polyorganosiloxane compounds can also contain polyether segments in the backbone.

9 Claims, No Drawings

POLYUREA- AND/OR POLYURETHANE-POLYORGANOSILOXANE COMPOUNDS

The invention relates to novel polyurea- and/or polyurethane-polyorganosiloxane compounds, processes for the preparation thereof, and their use and novel reactive 1- or 2-component systems and cured compositions therefrom.

Siloxane block copolymers containing quaternary ammonium structures are widely known. These can be on the one hand di-block copolymers of the AB type with siloxane and quaternary ammonium units (DE 3340708, EP 282720, U.S. Pat. No. 6,240,929, U.S. Pat. No. 6,730,766). On the other hand, tri-block copolymers which are based on the combination of siloxane, quaternary ammonium and polyether block units have been developed (WO 02/10256, WO 02/10257, WO 02/10259, WO 2004/090007, WO 03/078504, WO 2004/041912, WO 2004/042136). An essential advantage of these tri-block copolymers is that the structure thereof can be adapted flexibly and within very wide limits to suit concrete product requirements.

It is furthermore known to react siloxanes terminated with amino groups with hydrocarbon-based diisocyanates to give di-block copolymers containing urea groups (US 2006/036055). Polyether groups can be introduced only via urea-urea or urethane-urea bridges. Analogous urethane derivatives have likewise been described (US 2004/087752).

GB 1128642 discloses quaternary ammonium compounds containing urea and urethane groupings. The reaction of amino- or hydroxy-terminated siloxanes with diisocyanates leads to isocyanate-terminated intermediate stages, which then react, for example, with primary-tertiary di- or triamines, after which the tertiary amino group is quaternized. In all cases there are two urea groups between the siloxane block and quaternary group. It is furthermore possible e.g. to employ oligoethylene glycols as chain lengtheners. Isocyanate groups are used in the introduction of these, and are then no longer available for reaction with primary-tertiary di- or triamines, which leads to a reduction in the amount of quaternary ammonium groups. A disadvantage of this solution is therefore that flexible adaptation of the structure within wide limits to suit the concrete product requirements cannot take place.

It is furthermore known to react carbonate-functionalized siloxanes with hydrocarbons containing primary and secondary amino groups or hydroxyl groups to give silicones or corresponding esters containing urethane groups (U.S. Pat. No. 5,672,338, U.S. Pat. No. 5,686,547, DE 195 05 892).

It has likewise been proposed to use an unsymmetrically substituted carbonate as a linker group for the synthesis of siloxane-modified diquaternary compounds which contain urethane groups (WO 2005/058863).

Finally, the use of these unsymmetrically substituted carbonate linkers in the synthesis of polyurethane block copolymers containing siloxane units and with incorporated amine salt units has been described (C. Novi, A. Mourran, H. Keul, M. Möller, Macromol. Chem. Phys. 2006, 207, 273-286). A disadvantage of these compounds is that they only have pH-sensitive charges in the form of amine salts, which results in a reduced substantivity.

It is therefore an object of the invention to provide polyurea- and polyurethane-polyorganosiloxane block copolymers optionally containing quaternary ammonium groups, which on the one hand allow a flexible adaptation of the structure within wide limits to suit the concrete product requirements, and in which on the other hand essential product properties can be influenced under the influence of donor-acceptor interactions by the changed sequence of urea groups and/or urethane groups. Novel polymer compounds with novel properties which make possible uses which have not yet been opened up accessible are furthermore to be provided.

The present invention provides novel polyurea- and/or polyurethane-polyorganosiloxane compounds which can react from stable precursors to give the desired polyurea- and polyurethane-polyorganosiloxane compounds in a targeted manner when used. The novel polyurea- and/or polyurethane-polyorganosiloxane compounds can be prepared easily, reliably and in a targeted manner and have novel interesting properties.

The invention therefore relates to novel polyurea- and/or polyurethane-polyorganosiloxane compounds containing at least one structural element of the formula (1):

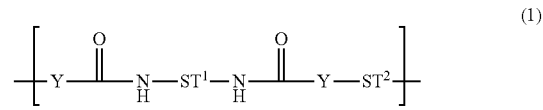

wherein
a) $ST^1$ and $ST^2$ independently of each other are chosen from divalent or more than divalent, straight-chain, cyclic or branched, saturated, unsaturated or aromatic, substituted or unsubstituted hydrocarbon radicals having up to 1,000 carbon atoms (wherein the carbon atoms of a polyorganosiloxane unit optionally present are not included in the total), which can contain one or more groups chosen from —O—, —C(O)—, —NH—, —NR³—,

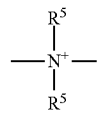

and a polydiorganosiloxane unit having 2 to 1,000 silicon atoms, wherein
$R^3$ is a straight-chain, cyclic or branched, saturated, unsaturated or aromatic hydrocarbon radical having up to 40 carbon atoms, which can contain one or more groups chosen from —O—, —C(O)— and —NH—, and
$R^5$ is a straight-chain, cyclic or branched, saturated, unsaturated or aromatic hydrocarbon radical having up to 100 carbon atoms, which can contain one or more groups chosen from —O—, —C(O)— and —NH—, or $R^5$ is a divalent radical which forms cyclic structures within the radicals $ST^1$ and/or $ST^2$, and wherein if a plurality of radicals $ST^1$ is present, these can be identical or different from one another, and if a plurality of radicals $ST^2$ is present, these can be identical or different from one another,
with the proviso that
the polyurea- and/or polyurethane-polyorganosiloxane compounds of the formula (1) include at least one polyorganosiloxane radical and at least one polyalkylene oxide radical,
or
b) $ST^1$ is chosen from divalent or more than divalent, straight-chain, cyclic or branched, saturated, unsaturated or aromatic, substituted or unsubstituted hydrocarbon radicals having up to 1,000 carbon atoms (wherein the carbon atoms of a polyorganosiloxane unit optionally present are not included in the total), which can contain one or more groups chosen from —O—, —C(O)—, —NH—, —NR³—,

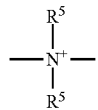

and a polydiorganosiloxane unit having 2 to 1,000 silicon atoms, wherein R³ and R⁵ are as defined above, and ST² is a radical of the formula (2)

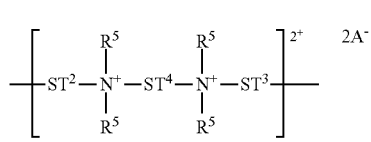

wherein

ST³ is a straight-chain or cyclic or branched, saturated or unsaturated or aromatic, substituted or unsubstituted hydrocarbon radical having 2 to 100 carbon atoms, which can contain one or more groups —O—, —C(O)—, —NH—, —NR³—, wherein R³ is as defined above, ST⁴ is a straight-chain or cyclic or branched, saturated or unsaturated or aromatic, substituted or unsubstituted hydrocarbon radical having 2 to 100 carbon atoms (wherein the carbon atoms of a polyorganosiloxane unit optionally present are not included in the total), which can contain one or more groups —O—, —C(O)—, —NH—, —NR³—, wherein R³ is as defined above, and a polydiorganosiloxane unit having 2 to 200 silicon atoms, and A⁻ is an organic or inorganic anion, with the proviso that at least one of the radicals ST¹, ST⁴ contains a polydiorganosiloxane radical, Y=—NR²— or —O—, wherein R² is hydrogen or a straight-chain, cyclic or branched, saturated, unsaturated or aromatic hydrocarbon radical having up to 40 carbon atoms, which can contain one or more groups chosen from —O—, —C(O)—, —NH— and —NR³—, wherein R³ is as defined above, or acid addition compounds and/or salts thereof.

According to the invention, the tell acid addition compounds means in particular salt-like compounds which are obtained by protonation of basic groups in the molecule, such as, in particular, amino groups optionally present, for example by reaction with inorganic or organic acids.

Salts of the compounds according to the invention result in particular from the formation of compounds containing quaternary ammonium groups, which contain, in particular, radicals

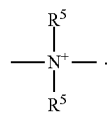

The case wherein R⁵ with ST⁴ can form a nitrogen-containing heterocyclic radical is also included according to the invention.

Substituents of the hydrocarbon radicals for ST¹, ST² ST³ or ST⁴ include preferably one or more, preferably one to three substituents, which are preferably chosen from the group which consists of: hydroxyl, halogen, such as fluorine or chlorine, and cyano.

The present invention therefore relates to two alternatives a) and b), which differ in particular in that alternative b) has quaternary ammonium groups, as a result of which these compounds have in particular a high substantivity or, respectively, adhesion and spreading on surfaces. Alternative b) therefore relates in particular to polyurea- and/or polyurethane-polyorganosiloxane compounds containing at least one structural element of the formula (3):

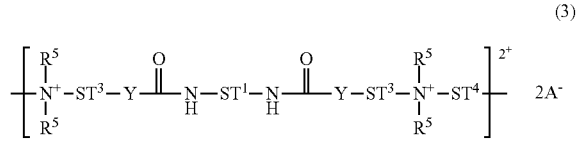

wherein

A⁻, R⁵, ST¹, ST³, ST⁴ and Y are as defined above.

Alternative a), on the other hand, relates in particular to polyurea- and/or polyurethane-polyorganosiloxane compounds containing at least one structural element of the formula (1):

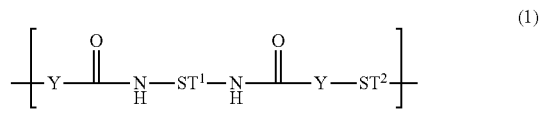

wherein

ST¹ and ST² independently of each other are chosen from divalent or more than divalent, straight-chain, cyclic or branched, saturated, unsaturated or aromatic, substituted or unsubstituted hydrocarbon radicals having up to 1,000 carbon atoms (wherein the carbon atoms of a polyorganosiloxane unit optionally present are not included in the total), which can contain one or more groups chosen from —O—, —C(O)—, —NH—, —NR³—,

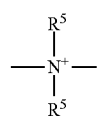

and a polydiorganosiloxane unit having 2 to 1,000 silicon atoms, wherein R³ and R⁵ are as defined above, and wherein if a plurality of radicals ST¹ is present, these can be identical or different from one another, and if a plurality of radicals $ST^2$ is present, these can be identical or different from one another, with the proviso that the polyurea- and/or polyurethane-polyorganosiloxane compounds include at least one polyorganosiloxane radical and at least one polyalkylene oxide radical. In this context, the polyorganosiloxane radicals and the polyalkylene oxide radicals are expediently contained in the radicals $ST^1$ and $ST^2$. Preferably, at least one of the radicals $ST^1$ contains a polyorganosiloxane radical and at least one of the radicals $ST^2$ contains a polyalkylene oxide radical, or at least one of the radicals $ST^2$ contains a polyorganosiloxane radical and at least one of the radicals $ST^1$ contains a polyalkylene oxide radical. However, it is also possible, although less preferred, for the radical $ST^1$ to contain at least one polyorganosiloxane radical and at least one polyalkylene oxide radical. And it is also possible, although less preferred, for the radical $ST^2$ to contain at least one polyorganosiloxane radical and at least one polyalkylene oxide radical.

The polyalkylene oxide radical such as is used according to the invention results from random or block-like alkylene oxide homo- or copolymers, in particular based on ethylene oxide and/or propylene oxide and/or butylene oxide. The number of alkylene oxide units in the polyalkylene oxide radical is, for example, 2 to 1,000. Those polyalkylene oxide radicals which are based on ethylene oxide/propylene oxide copolymers, in particular random ethylene oxide/propylene oxide copolymers with 2 to 100 ethylene oxide and propylene oxide units, the content of ethylene oxide units in particular being greater than that of propylene oxide units, are particularly preferred.

Copolymers which are particularly preferred are random copolymers of ethylene oxide and propylene of the following formula (4)

(4)

wherein a can be from 0 to 100 and b can be from 2 to 1,000 and a+b can be from 2 to 1,100.

These radicals are preferably alkylene-terminated, such as those of the formula (5)

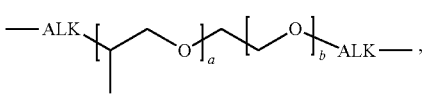

(5)

wherein the radicals 'ALK' can be identical or different and are chosen from divalent straight-chain or branched alkylene radicals having 1 to 40 carbon atoms, which can optionally be substituted, and a and b are as defined above.

In a preferred embodiment of the invention, $ST^1$ is a radical of the above formula:

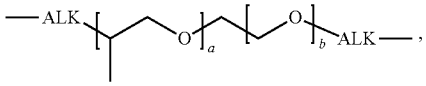

wherein 'ALK' and a and b are as defined above. The introduction of such radicals $ST^1$ is in particular by the use of isocyanate-terminated polyalkylene oxide compounds.

In a further preferred embodiment, $ST^4$ represents a group containing a polyalkylene oxide radical, introduction of the group being achieved, in particular, by the use of haloalkyl-terminated polyalkylene oxide compounds as quaternizing agents, as described in still more detail below.

That is to say in this variant at least one hydrophobic polyorganosiloxane radical is present in the molecule, in addition to at least one hydrophilic polyalkylene oxide radical. The chain length and therefore the molecular weight of the block or co- or block terpolymer can be controlled via the molar ratio of these radicals or the chain length of the radicals. Either the reactive groups of the reactive precursor employed in excess are formed as chain end groups. These are NCO—, OH—, $NR_2$— and/or epoxy groups or reaction products of reactive groups with hydrogen-active compounds which are present or added in a targeted manner, chosen from monofunctional alcohols, thiols, amines, epoxides or acids. The molar ratio and the molecular weight influence properties such as, in particular, adhesion to surfaces, hydrophilicity, softness, low temperature flexibility, spreading properties, gas permeability etc., which can therefore be tailor-made.

The polyurea- and/or polyurethane-polyorganosiloxane compounds according to the invention preferably contain at least one polydiorganosiloxane structural element of the formula (6):

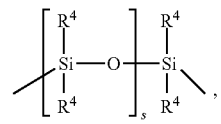

(6)

wherein $R^4$ is a straight-chain, cyclic or branched, saturated, unsaturated or aromatic, substituted or unsubstituted hydrocarbon radical having up to 20 C atoms, and s=1 to 999.

Preferably, $R^4$ is a $C_1$ to $C_{20}$, more preferably $C_1$ to $C_9$, straight-chain or cyclic or branched, saturated or unsaturated or aromatic hydrocarbon radical, particularly preferably methyl and phenyl, and s is 1 to 199, more preferably 1 to 99.

The polyurea- and/or polyurethane-polyorganosiloxane compounds according to the invention still more preferably contain at least one polydiorganosiloxane structural element of the formula (6'):

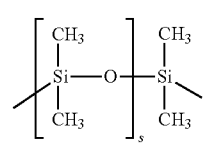

(6')

wherein s is as defined above.

The polyurea- and/or polyurethane-polyorganosiloxane compounds according to the invention contain on average preferably at least two, more preferably at least three structural elements of the formula (1).

The polyurea- and/or polyurethane-polyorganosiloxane compounds according to the invention preferably contain on average at least two, preferably at least three polydiorganosiloxane structural elements of the formula (6) or (6').

In a preferred embodiment of the invention, the polyurea- and/or polyurethane-polyorganosiloxane compounds contain divalent radicals $ST^1$, $ST^2$, $ST^3$ and $ST^4$, so that the polyurea- and/or polyurethane-polyorganosiloxane compounds are linear in structure. In certain uses, however, it is preferable for branched polyurea- and/or polyurethane-polyorganosiloxane compounds to be formed by using more than in divalent radicals, in particular tri- or tetravalent radicals $ST^1$, $ST^2$, $ST^3$ and $ST^4$. Compounds which are elastomeric or thermosetting and also improved with respect to their resistance to solvents can thereby be obtained. Preferably, compounds with divalent radicals $ST^1$, $ST^2$, $ST^3$ and $ST^4$ and more than divalent radicals $ST^1$, $ST^2$, $ST^3$ and $ST^4$ are prepared here.

In a further preferred embodiment of the invention, the compounds are pure polyurethane-polyorganosiloxane compounds, i.e. Y is NH or $NR^2$, wherein $R^2$ is as defined above. These are particularly suitable as plasticizers and for the preparation of gas-permeable membranes and low temperature impact modifiers.

The polyurea- and/or polyurethane-polyorganosiloxane compounds according to the invention preferably contain at least one radical of the formula:

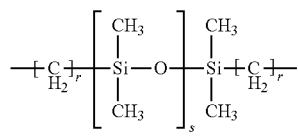

wherein s is as defined above, r is from 1 to 12, preferably 1 or 3.

The polyurea- and/or polyurethane-polyorganosiloxane compounds according to the invention can preferably be obtained by a process which includes the reaction of a compound of the formula

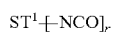

wherein $ST^1$ is as defined above, and r is ≥2, with a compound of the formula

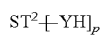

wherein $ST^2$ is as defined above, and p is ≥2, with the proviso that
the polyurea- and/or polyurethane-polyorganosiloxane compounds include at least one polyorganosiloxane radical and at least one polyalkylene oxide radical, and in particular the radical $ST^1$ includes a polyorganosiloxane radical and the radical $ST^2$ includes a polyalkylene oxide radical, or
the radical $ST^2$ includes a polyorganosiloxane radical and the radical $ST^1$ includes a polyalkylene oxide radical.

In a preferred embodiment of this process, r and p=2, i.e. linear polyurea- and/or polyurethane-polyorganosiloxane compounds are formed.

Y is preferably or —$NR^2$—, so that polyurea-polyorganosiloxane compounds are formed.

Compounds which are preferably employed in the process according to the invention for the preparation of the polyurea- and/or polyurethane-polyorganosiloxane compounds are those of the formula

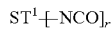

which are chosen from
aliphatic, di- or polyvalent, straight-chain or branched polyisocyanates having up to 15 carbon atoms, for example hexamethylene-diisocyanate,
aliphatic, di- or polyvalent, cyclic polyisocyanates having up to 15 carbon atoms, such as, for example

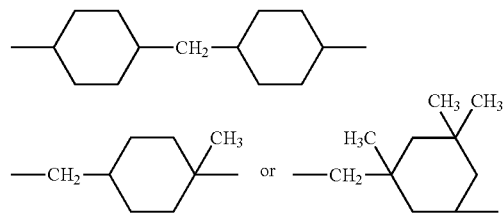

di- or polyvalent, aromatic polyisocyanates having up to 15 carbon atoms, for example based on 2,4-toluyl, 2,6-toluyl, bis-phenylmethane and naphthylene structures, such as

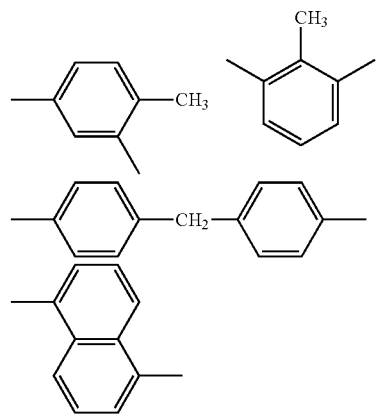

more complex polyisocyanates, such as, for example
isocyanate-terminated polyethers, preferably ethylene oxide- and propylene oxide-based polyethers, for example prepared from primary amino-terminated polyethers of the Jeffamine® type, for example of the ED and T series (Huntsman Corp.),
isocyanate-terminated polyamides,
isocyanate-terminated polyureas,
isocyanate-terminated polyurethanes,
isocyanatoalkyl-functionalized polyorganosiloxanes, such as polyisocyanates of higher functionality which are derived from polyorganosiloxanes which carry primary amino groups and have primary amino functions which are arranged comb-like and optionally in the α,ω) position.
Compounds of the Formula

are preferably attributed to primary amines and can be produced from these by means of known synthesis methods (Organikum, 17th edition, VEB Deutscher Verlag der Wissenschaften, Berlin 1988, p. 427-428). These are preferably here the reaction of primary amines or corresponding amine hydrochlorides with phosgene.

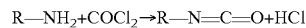

The isocyanate groups such as are used according to the invention can be blocked, as is well-known to the person skilled in the art. Whenever the term "isocyanate" or the radical —NCO is mentioned in the present invention, this always also includes blocked isocyanate groups, wherein the isocyanate group is present in a form blocked in a manner known per se. In this manner, for example, reactive 1-component systems of which the reactivity or pot life is reduced sufficiently, as described in still more detail below, can be provided. The blocking agents are preferably chosen from the group which consists of substituted phenols, oximes, pyrazoles, dimalonates, lactams, triazoles of other keto esters, for example compounds such as methyl ethyl ketoxime, 3,5-dimethyl-1,2-pyrazole, diethyl malonate, ε-caprolactam, 1,2,4-triazole or ethyl acetoacetate are preferred. The reactivity can thereby be raised to a higher temperature level in various ways, in order to control the pot life or stoving temperature.

With respect to variant a) of the polyurea- and/or polyurethane-polyorganosiloxane compounds according to the invention, the radical $ST^1$ in the formula

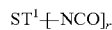

preferably contains either a polyalkylene oxide group or a polyorganosiloxane group, and the radical $ST^2$ in the compound of the formula $ST^2\text{---}[YH]_p$ contains a polyalkylene oxide group or a polyorganosiloxane group, so that either $ST^1$ or $ST^2$ is a polyalkylene oxide group and $ST^1$ or $ST^2$ contains a polyorganosiloxane group.

Particularly preferably, $ST^1$ contains a polyalkylene oxide group and $ST^2$ contains a polyorganosiloxane group.

As the compound of the formula

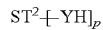

those which are preferably used are those chosen from:
aliphatic, divalent or polyvalent, straight-chain or branched polyols or polyamines having up to 15 carbon atoms, for example hexamethylenediamine or -diol,
aliphatic, divalent or polyvalent, cyclic polyols or polyamines having up to 15 carbon atoms, for example based on biscyclohexylmethane structures

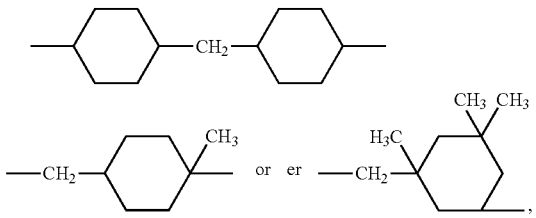

di- or polyvalent, aromatic polyols or polyamines having up to 15 carbon atoms, for example, based on 2,4-toluyl, 2,6-toluyl, bis-phenylmethane and naphthylene structures

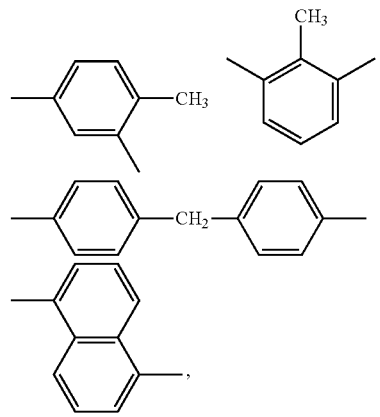

in particular hexamethylenediamine, phenylenediamine, toluenediamines, cyclohexanediamine, ethylenediamine and propylenediamine,
divalent or more than divalent primary and/or secondary amines or alcohols, such as, for example, $N(CH_2CH_2NH_2)_3$, diethylenetriamine, dipropylene-triamine and higher oligomers, glycerol and alkoxylated derivatives thereof,
more complex, divalent or more than divalent polyamines or polyols, such as primary and secondary amino- or hydroxy-functionalized prepolymers, which can likewise be of higher functionality, such as, for example,
  primary or secondary amino- or hydroxyl-terminated polyethers, preferably ethylene oxide- and propylene oxide-based polyethers, for example primary or secondary amino-terminated polyethers of the Jeffamine® type, for example of the ED and T series (Huntsman Corp.),
  $NH_2$-terminated polyamides,
  $NH_2$-terminated polyureas,
  $NH_2$-terminated polyurethanes,
  OH-terminated polyureas,
  OH-terminated polyurethanes,
  OH-terminated polyesters,
  α,ω-primary or secondary amino- or hydroxyalkyl- or hydroxypolyether alkyl-functionalized polyorganosiloxanes, such as polyorganosiloxanes of higher functionality which carry primary or secondary amino or hydroxyalkyl or hydroxypolyether alkyl groups and have amino or hydroxyl functions which are arranged comb-like and optionally in the α,ω position.
Compounds $ST^2\text{---}[YH]_p$ which are particularly preferably used are those which contain either a polyorganosiloxane radical or a polyalkylene oxide radical, in each case as described above.

The polyurea- and/or polyurethane-polyorganosiloxane compounds according to Do variant b), that is to say in particular those of the formula (3)

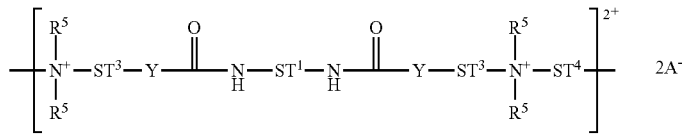

(3)

wherein
A⁻, $R^5$, $ST^1$, $ST^3$, $ST^4$ and Y are as defined above
are preferably obtained by a process which includes the reaction of a compound of the formula $ST^1$—[NCO]$_r$, wherein $ST^1$ is as defined above, with a compound of the formula

HY-$ST^3$-N$R^5{}_2$, wherein Y, $ST^3$ and $R^5$ are as defined above,
and then reaction of the reaction product obtained with a compound of the formula

Q-$ST^{4V}$-Q, wherein Q is a radical which is capable of alkylation of an amino group, and $ST^{4V}$, together with the molecular part originating from Q after the quaternization reaction, forms the radical $ST^4$.

The compounds of the formula

HY-$ST^3$-N$R^5{}_2$, used here are preferably chosen from
primary-tertiary or secondary-tertiary diamino structures, such as, for example, N,N-dimethylpropylenediamine and N-methylpiperazine,
primary-secondary diamines, for example aminoethylethanolamine, or amines of higher functionality, such as N,N,N',N'-tetramethyldipropylenetriamine and N,N,N',N'-tetramethyldiethylenetriamine or
tertiary amino-functionalized alcohols, e.g. HOCH$_2$CH$_2$N(CH$_3$)$_2$.

The radicals Q which are capable of quaternization or, respectively, alkylation of the amino groups are preferably chosen from epoxy groups, halocarboxylic acid ester groups and haloalkyl groups. The following example serves to illustrate the radical $ST^{4V}$:

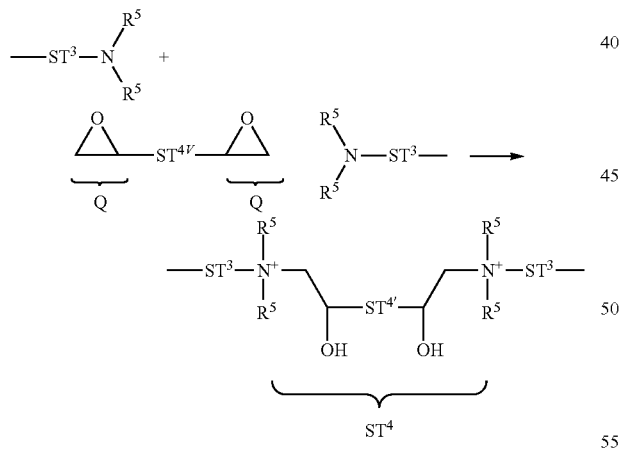

$ST^4$ is thus formed from $ST^{4V}$ and from the molecular parts resulting from the epoxy groups.

The compounds of the formula

Q-$ST^{4V}$-Q, used as quaternizing agents are preferably chosen from:
divalent or optionally also more than divalent alkylating agents containing epoxy groups, halocarboxylic acid ester groups or haloalkyl groups, particularly preferably hydrocarbon-based α,ω-epoxy- or halogen-functionalized substances, specifically
hydrocarbon diepoxides,
for example vinylcyclohexene diepoxide,
epichlorohydrin,
epoxy-terminated polyethers, preferably ethylene oxide- and propylene oxide-based polyethers, for example glycidyl-terminated polyethers,
epoxy-terminated polyesters,
epoxy-terminated polycarbonates,
halogen-functionalized hydrocarbon derivatives, preferably chlorides and bromides,
for example hydrocarbon dihalides,
halogen-terminated polyethers, preferably ethylene oxide- and propylene oxide-based polyethers,
haloalkylcarboxylic acid esters obtainable from hydrocarbon diols and polyethers, preferably ethylene oxide- and propylene oxide-based polyethers, specifically chloroacetic acid esters, chloropropionic acid esters and chlorobutanoic acid esters of hydrocarbon diols and polyethers,
difunctional acid alkoxylates converted into corresponding glycidyl, halogen or haloalkylcarboxylic acid ester derivatives, for example succinic acid alkoxy derivatives,
more complex α,ω-epoxy- or halogen-terminated compounds which are derived from α,ω-hydroxy-functionalized prepolymers, preferably the reaction products of diols with diisocyanates, OH-terminated polyethers, preferably ethylene oxide- and propylene oxide-based polyethers with diisocyanates, OH-terminated polyesters, OH-terminated polycarbonates, which are converted into the corresponding α,ω-halocarboxylic acid esters, specifically chloroacetic acid esters, chloropropionic acid esters and chlorobutanoic acid esters,
compounds containing polyorganosiloxane blocks, preferably α,ω-epoxy-terminated polyorganosiloxanes, preferably α,ω-glycidyl- and epoxycyclohexyl-terminated polyorganosiloxanes, terminated polyorganosiloxanes, preferably chloropropyl- and chloropropenyl-terminated polyorganosiloxanes, α,ω-halocarboxylic acid ester-terminated polyorganosiloxanes, preferably esters of chloroacetic acid, chloropropionic acid and chlorobutanoic acid, α,ω-halocarboxylic acid ester-terminated polyether-polyorganosiloxanes, preferably esters of chloroacetic acid, chloropropionic acid and chlorobutanoic acid, α,ω-epoxy- or halogen-functionalized polyorganosiloxane prepolymers, which can preferably be obtained from the corresponding α,ω-hydroxyalkyl or α,ω-hydroxypolyether-terminated siloxane prepolymers,
hydrocarbon-based or siloxane-based substances of higher functionality with more than two of the epoxy or halogen functions dealt with above, for example the glycidyl or chloroacetic acid ester derivatives of glycerol, pentaerythritol, sorbitol, and of ethoxylates/propoxylates thereof,
glycidyl or chloroacetic acid ester derivates of acid alkoxylates of higher functionality, for example derived from trimellitic acid or pyromellitic acid, and
siloxane-based substances of higher functionality with α,ω- and/or comb-like epoxy or halogen, preferably halocarboxylic acid ester substitution, wherein the functionality of these hydrocarbon-based or siloxane-based substances of higher functionality is greater than 2.

The introduction of siloxane blocks into the unit $ST^2$ is carried out, for example, starting from α,ω-primary or secondary amino- or hydroxyalkyl- or hydroxypolyether alkyl-functionalized polyorganosiloxanes. The preparation of the corresponding α,ω-primary or secondary aminoalkyl- or hydroxyalkyl- or hydroxypolyether alkyl-functionalized polyorganosiloxanes is prior art (Silicone, Chemie and Technologie, Vulkan Verlag Essen 1989, p. 85-90).

α,ω-Primary or secondary aminoalkyl- or hydroxyalkyl- or hydroxypolyether alkyl-functionalized prepolymers which are preferably accessible by reaction of α,ω-primary or secondary aminoalkyl-terminated siloxanes with diisocyanates, α,ω-hydroxyalkyl-terminated siloxanes with diisocyanates, α,ω-hydroxypolyether-terminated siloxanes with diisocyanates can furthermore be employed.

It is furthermore within the context of the invention to employ polyorganosiloxanes of higher functionality carrying primary or secondary amino groups or hydroxyalkyl or hydroxypolyether alkyl groups for formation of the hydrocarbon radical $ST^2$. These siloxanes functionalized in a comb-like manner and optionally in the α,ω position are likewise known from the prior art.

In the case of quaternized polyurea- and/or polyurethane-polyorganosiloxane compounds, the isocyanate-terminated $ST^1$ intermediates are first reacted with compounds which contain the element $ST^3$. Quaternization with introduction of the element $ST^4$ is then carried out.

The reaction partners containing $ST^3$ are preferably substances which have primary-tertiary or secondary-tertiary diamino structures, such as, for example, N,N-dimethylpropylenediamine. The similarly preferred use of e.g. N-methylpiperazine includes the possibility that cyclic ST structures can form. Alternatively, tertiary amino-functionalized alcohols, e.g. $HOCH_2CH_2N(CH_3)_2$, can be used for introduction of $ST^3$.

A prerequisite of the use of such $ST^3$ units with diamino structures is the simultaneous use of polyfunctional, in particular difunctional quaternizing agents which introduce $ST^4$. Otherwise, no chain formation is possible.

The formation of the $ST^2$ structural element of the formula:

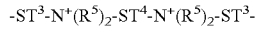

is carried out in this manner.

The use of primary-secondary diamines for introduction of $ST^3$ is also possible.

After the build up of the chain, amino groups which remain can then optionally be alkylated.

Examples of amines of higher functionality for producing branched $ST^3$ structures are:
N,N,N',N'-tetramethyldipropylenetriamine (Jeffcat ZR50B Huntsman) N,N,N',N'-tetramethyldiethylenetriamine.

The reaction partners forming the $ST^4$ units are poly-, in particular difunctional alkylating agents, which preferably have epoxy groups, halocarboxylic acid ester groups and haloalkyl groups.

In a preferred embodiment, the partners containing $ST^4$ are hydrocarbon-based α,ω-epoxy- or halogen-functionalized substances.

It is likewise within the context of the invention to convert difunctional acid alkoxylates into corresponding glycidyl, halogen or halocarboxylic acid ester derivatives and to employ them according to the invention. These are derived, for example, from succinic acid.

The synthesis of the particularly preferred chlorocarbonic acid esters is carried out in a known manner (Organikum, Organisch-Chemisches Grundpraktikum, 17th edition, VEB Deutscher Verlag der Wissenschaften, Berlin 1988, p. 402-408) by reaction of the diol component with the corresponding halocarboxylic acid anhydrides or halocarboxylic acid chlorides.

In a further embodiment, the hydrocarbon radicals $ST^4$ are more complex α,ω-epoxy- or halogen-terminated structures which are derived from α,ω-hydroxy-functionalized prepolymers.

These α,ω-amino-functionalized prepolymers are preferably the reaction products of
diols with diisocyanates
OH-terminated polyethers, preferably ethylene oxide- and propylene oxide-based polyethers with diisocyanates
OH-terminated polyesters
OH-terminated polycarbonates.

In a preferred embodiment, these α,ω-hydroxy-functionalized prepolymers are converted into the corresponding α,ω-halocarboxylic acid esters, specifically chloroacetic acid esters, chloropropionic acid esters and chlorobutanoic acid esters.

The introduction according to the invention of siloxane blocks into $ST^4$ is preferably carried out via
α,ω-epoxy-terminated siloxanes, preferably α,ω-glycidyl- and epoxycyclohexyl-terminated siloxanes,
α,ω-haloalkyl-terminated siloxanes, preferably chloropropyl- and chloropropenyl-terminated siloxanes,
α,ω-halocarboxylic acid ester-terminated siloxanes, preferably esters of chloroacetic acid, chloropropionic acid and chlorobutanoic acid.
α,ω-halocarboxylic acid ester-terminated polyether-siloxanes, preferably esters of chloroacetic acid, chloropropionic acid and chlorobutanoic acid.

The preparation of the α,ω-epoxy-terminated siloxanes and α,ω-haloalkyl-terminated siloxanes entering into $ST^4$ is described in the prior art (Silicone, Chemie and Technologie, Vulkan Verlag Essen 1989, p. 85-90 and 120).

The preparation of α,ω-halocarboxylic acid ester-terminated siloxanes can be carried out analogously to the procedure according to WO 02/10256, Example 1. In this, SiH-siloxanes are reacted with halocarboxylic acid esters of olefinically or acetylenically unsaturated alcohols.

The preparation of α,ω-halocarboxylic acid ester-terminated polyether-siloxanes can be carried out analogously to WO 02/10257, Example 1. In this, SiH-siloxanes are reacted with halocarboxylic acid esters of olefinically or acetylenically unsaturated polyethers. Alternatively, it is possible to react polyether-siloxanes with halocarboxylic acids or anhydrides or acid chlorides thereof (U.S. Pat. No. 5,153,294, U.S. Pat. No. 5,166,297).

In a further embodiment, the introduction of siloxane blocks into $ST^4$ is carried out via α,ω-epoxy- or halogen-functionalized siloxane prepolymers, which can preferably be obtained from the corresponding α,ω-hydroxyalkyl or α,ω-hydroxypolyether-terminated siloxane prepolymers.

These OH-terminated siloxane-containing prepolymers are preferably prepared by reaction of
α,ω-hydroxyalkyl-terminated siloxanes with diisocyanates,
α,ω-polyether-terminated siloxanes with diisocyanates,
and are then converted into the epoxy and halogen derivatives. The α,ω-halocarboxylic acid-functionalized siloxane prepolymers which are accessible by esterification with e.g. the anhydrides and acid chlorides represent a preferred embodiment. It is furthermore within the context of the invention to employ hydrocarbon-based or siloxane-based substances of higher functionality for formation of the radical $ST^4$. These materials contain more than two of the epoxy or halogen functions dealt with above.

Examples of hydrocarbon-based substances of higher functionality are the glycidyl or chloroacetic acid ester derivatives of glycerol, pentaerythritol, sorbitol, and of ethoxylates and/or propoxylates thereof. It is likewise within the context of the invention to convert acid alkoxylates of higher functionality into corresponding glycidyl or chloroacetic acid ester derivatives and to employ them according to the invention. These are derived, for example, from trimellitic acid or pyromellitic acid.

Suitable siloxane-based substances of higher functionality with α,ω- and/or comb-like epoxy or halogen, preferably halocarboxylic acid ester substitution can be obtained, for example, from hydroxy-functional precursors, which are accessible by addition of allyl alcohol, butynediol and the alkoxylates of allyl alcohol or butynediol on to corresponding SiH-siloxanes. Alternatively, for example, unsaturated epoxy- or halocarboxylic acid ester-functional precursors can be added on to corresponding SiH-siloxanes.

It is an essential feature that the functionality of these hydrocarbon-based or siloxane-based substances of higher functionality is greater than 2.

It is furthermore within the context of the invention to employ monofunctional hydrocarbon-based or siloxane-based substances for formation of the radical $ST^4$. These materials contain one of the epoxy or halogen functions dealt with above.

Examples of monofunctional hydrocarbon-based substances are the glycidyl or chloroacetic acid ester derivatives of alkanols, for example ethanol, 2-propanol, dodecanol and octadecanol, alkenols, for example allyl alcohol, hexenol, oleyl alcohol, and alkynols, for example propynol, and the alkoxylates, specifically ethoxylates/propoxylates, of the monofunctional alcohols mentioned. It is likewise within the context of the invention to convert fatty acid alkoxylates into corresponding glycidyl or chloroacetic acid ester derivatives and to employ them according to the invention.

Suitable monofunctional siloxane-based substances with epoxy or halogen, preferably halocarboxylic acid ester substitution are known e.g. from WO 02/10256. They can be obtained, for example, from unsaturated epoxy- or halocarboxylic acid ester-functional precursors, which can be added on to corresponding SiH-siloxanes.

Depending on their nature, these monofunctional hydrocarbon-based or siloxane-based $ST^4$ precursors are added in order to regulate the molecular weight of the polymers formed and, where appropriate in cooperation with the $ST^4$ precursors of higher functionality, to control the degree of branching of the polymer chains.

If epoxy-containing substances are used for introduction of $ST^4$ groups, acid is added in stoichiometric amounts in a manner known from the prior art. The anions are inorganic anions, such as halide, specifically chloride, and organic anions, such as carboxylate, specifically $C_2$ to $C_{18}$-carboxylate, alkyl polyether-carboxylate, alkyl-sulfate, specifically methosulfate, sulfonate, specifically alkylsulfonate and alkylarylsulfonate, very specifically toluylsulfonate.

As a result of the entire reaction sequence shown, quaternized or non-quaternized polyurea- and/or polyurethane-polyorganosiloxane compounds which have siloxane units at least in one of the structural elements $ST^1$ and/or $ST^2$ are obtained.

The reactions of diisocyanates with the amino- or hydroxy-functional $ST^2$, $ST^3$ and $ST^4$ precursors are preferably carried out in the range of from room temperature to 160° C., preferably to 140° C. The reaction times are a few minutes to some hours.

It is within the context of the invention to carry out the entire reaction sequence or individual part steps without a solvent or in the presence of solvents. Preferred solvents are typical lacquer solvents, such as methoxypropyl acetate, butyl acetate or toluene.

The present invention provides not only novel polyurea- and/or polyurethane-polyorganosiloxane compounds, but in particular also reactive 1- or 2-component systems suitable for the formation thereof. These systems contain in particular at least one compound of the formula

wherein $ST^1$ is as defined above, and r is ≥2, wherein the isocyanate groups can optionally be blocked in a manner known per se, and at least one compound of the formula

wherein $ST^2$ is as defined above, and p is ≥2, with the proviso that the radical $ST^1$ includes a polyorganosiloxane radical and the radical $ST^2$ includes a polyalkylene oxide radical, or the radical $ST^2$ includes a polyorganosiloxane radical and the radical $ST^1$ includes a polyalkylene oxide radical, and optionally fillers, pigments, further binders, auxiliary substances, solvents.

As already demonstrated above, the compounds of the formula

can be either free isocyanate compounds, which are used in particular in 2-C systems, or blocked isocyanate compounds, which can be used in particular in 1-C systems.

The invention therefore furthermore provides cured compositions which are obtainable from the reactive systems, in particular the reactive 1- or 2-component systems, by curing, in particular at elevated temperatures of, for example, more than 60° C., more preferably more than 100° C.

A further reactive 1- or 2-component system in the curing of which the formation of polyurea- and/or polyurethane-polyorganosiloxane compounds according to variant b) which have diquaternary recurring units occurs contains at least one reaction product from at least one compound of the formula

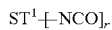

wherein $ST^1$ is as defined above and the —NCO groups can be blocked, and at least one compound of the formula

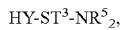

wherein Y, $ST^3$ and $R^5$ are as defined above, and at least one compound of the formula

wherein Q is a radical which is capable of alkylation of an amino group, and $ST^{4V}$, together with the molecular part originating from Q after the quaternization reaction, forms the radical $ST^4$, and optionally fillers, pigments, further binders, auxiliary substances, solvents.

The invention therefore also relates to cured compositions which are obtainable by curing these reactive 1- or 2-component systems.

The invention furthermore also relates to the use of the polyurea- and/or polyurethane-polyorganosiloxane compounds according to the invention or of the reactive 1- or 2-component systems according to the invention or of the cured compositions obtained therefrom, for example, for the preparation of coatings, agents for modification of surfaces, elastomers, thermosets, and shaped articles therefrom, adhesives, such as hot-melt adhesives, sealing materials, in particular for films, and film welds and reactive adhesives, as primers for metal and plastics surfaces, polymer additives, detergent additives, rheological agents, cosmetic, and agents for modification of fibres.

The polyurea- and/or polyurethane-polyorganosiloxane compounds according to the invention or the reactive 1- or 2-component systems according to the invention or the cured compositions obtained therefrom are preferably used in the preparation of coatings or as or in agents for modification of hard surfaces, such as, for example, of glass, ceramic, tiles, concrete and metal, in particular steel parts, such as automobile bodies and ships' hulls, for the preparation of primers for bonding silicone elastomers with other substrates, such as metal, in particular steel, aluminium, glass, plastics, such as epoxy resins, polyamides, polyphenylene sulfides, polyesters, such as polyterephthalates, for the preparation of thermoplastics, such as polyolefins, polyamides, polyurethanes, poly(meth)acrylates, polycarbonates, polyesters, whether the thermoplastics are formed from the polyurea- and/or polyurethane-polyorganosiloxane compounds according to the invention or these are used as additives in the plastics, for the preparation of low temperature impact modifiers, for the preparation of adhesives and sealants, for the preparation of elastomers, of thermoplastic elastomers, such as, for example, for the production of cable sheathings, hoses, seals, keyboard mats, membranes, such as selectively gas-permeable membranes, in coatings, such as antifouling coatings, non-stick coatings, as fabric-compatible coverings, in flame-retardant coverings and in biocompatible materials, in cosmetics, such as e.g. as an encapsulating material, in body care compositions, as lacquer additives, as an auxiliary substance in detergents, in defoamer formulations and in textile processing, for modification of resins or for modification of bitumen, as a packaging material for electronic components, as an insulating or shielding material, as a sealing material in hollow spaces with formation of condensation water, such as in aircraft, ships, automobiles, as additives for polishing, cleaning or care compositions, as an additive for body care compositions, as a coating material for wood, paper and cardboard, as mould release agents, as or in biocompatible materials in medical uses, such as contact lenses, as a coating material for textile fibres or textile fabric, as a coating material for natural substances, such as e.g. leather and furs, as a material for membranes and as a material for photoactive systems, e.g. for lithography processes, optical data protection or optical data transmission.

The invention furthermore relates to the use of the polyurea- and/or polyurethane-polyorganosiloxane compounds, of the reactive 1- or 2-component systems and of the cured compositions therefrom for the preparation of viscosity regulators, antistatic agents, of mixing components for silicone rubbers which can be crosslinked to elastomers peroxidically or by hydrosilylation (platinum catalysis), and there lead to modification of surface properties, to modification of the diffusion of gases, liquids etc., or modify the swelling properties of the silicone elastomers, in softeners for textile fibres, for treatment of the textile fibres before, during and after washing, in compositions for modification of natural and synthetic fibres, such as, for example, hair, cotton fibres and synthetic fibres, such as polyester fibres and polyamide fibres and blended fabrics, of textile finishing compositions, in detergent-containing formulations, such as in detergents and cleaning compositions based on anionic, nonionic and/or cationic surfactants, specifically in solid or liquid detergent formulations in contents of from about 0.1 to 10 wt. %, based on the total amount of the formulation, in cosmetic formulations and fibre treatment formulations, such as to textile care compositions, in contents of from about 0.1 to 50 wt. %, based on the total amount of the formulation.

The invention furthermore relates to the use of the polyurea- and/or polyurethane-polyorganosiloxane compounds or of the reactive 1- or 2-component systems and of the cured compositions therefrom for treatment and finishing of hard surfaces, such as glass, ceramic, tiles, plastics surfaces, metal surfaces, lacquer surfaces, specifically ship hulls and automobile bodies, quite specifically also in dryer formulations for mechanical washing of automobiles, as adhesives or primers, preferably for bonding silicone elastomers with other substrates, such as steel, aluminium, glass, epoxy resin, polyamide, as modifiers, e.g. low temperature impact modifiers and polarity modifiers, for hydrocarbon-based polymers and silicone-based elastomer systems based on peroxidic and Pt-catalysed crosslinking.

The invention furthermore relates to the use of the polyurea- and/or polyurethane-polyorganosiloxane compounds or of the reactive 1- or 2-component systems and of the cured compositions therefrom for treatment of natural and synthetic fibres, for example cotton, wool, polyester- and polyamide-based synthetic fibres, specifically in the form of textiles, in specific compositions for fibre treatment, in particular in detergent formulations containing anionic, nonionic and cationic surfactants, wherein the compounds according to the invention can be incorporated directly into the detergent or can be metered in separately as the washing process runs or after the washing process, as a constituent of separate softener systems, specifically based on cationic surfactants, after washing of fibres and textiles, as an ironing aid and an agent for preventing or reversing creases in textiles, for finishing fibres, specifically for the first finishing and treatment of, for example, cotton, wool, polyester- and polyamide-based synthetic fibres, specifically in the form of textiles, paper and wood.

The invention furthermore relates to the use of the polyurea- and/or polyurethane-polyorganosiloxane compounds or of the reactive 1- or 2-component systems and of the cured compositions therefrom in cosmetic systems for treatment of hair and skin, preferably as the pure substance, in particular aqueous or aqueous/organic solutions, mixtures, emulsions or microemulsions in the form of liquids, creams or pastes of differing viscosity, in cosmetic formulations for treatment of keratin-containing substrates, such as e.g. human and animal hair or skin, as an alcoholic or polyalcoholic solution or as a clear, cloudy, white emulsion or microemulsion, for example in so-called "rinse-off" compositions, such as e.g. "2-in-1" shampoos, "body wash" formulations and hair rinses for treatment of hair during and after cleansing or after colouring or treatment of hair before bleaching, curling or straightening, and in so-called "leave-in" compositions, such as hair treatments, care creams, hairdressing creams, hair gels, hair styling products, hair setting compositions, hair sprays, pump sprays, blow-waving compositions and blow-drying compositions, furthermore in permanent, semipermanent and temporary hair colouring compositions, in compositions for increasing the volume, the combability and the shine, and for reducing washing out of the colour from and out of coloured keratin-containing substrates, such as e.g. human and animal hair.

The polyurea- and/or polyurethane-polyorganosiloxane compounds according to the invention or the reactive 1- or 2-component systems and the cured compositions therefrom are preferably on solid carriers in non-transparent fabric softener dispersions or fabric softener emulsions or transparent microemulsions or solutions, in laundry freshener systems.

In cosmetic formulations for hair, in this context the polyurea- and polyurethane-polyorganosiloxane compounds according to the invention can exert in particular the function of so-called conditioning agents ("conditioners"), i.e. in particular favourably influence the properties of hair, such as softness, shine, fullness, combability etc., it also being possible for them to be used, in particular, in combination with other conventional conditioning agents, such as e.g. poly-alpha-olefins, fluorinated oils, fluorinated waxes, fluorinated rubbers, carboxylic acid esters having at least 10 carbon atoms, cationic polymers, silicones which are insoluble or soluble in the medium of the formulation, mineral oils, plant oils and animal oils and mixtures thereof, as described, for example, in WO 99/009939.

In this context, the expression "for the preparation of" as used above also includes the case where the polyurea- and/or polyurethane-polyorganosiloxane compounds according to the invention are used by themselves for the use mentioned. That is to say, for example, the polyurea- and/or polyurethane-polyorganosiloxane compounds according to the invention can be used themselves directly as low temperature impact modifiers. However, they can also be provided suitably to a certain extent as an additive in the said uses beforehand, for example by mixing, compounding, preparation of masterbatches.

The present invention furthermore relates to novel detergent formulations, cosmetic formulations, fibre treatment formulations which contain the polyurea- and/or polyurethane-polyorganosiloxane compounds according to the invention.

The polyurea- and/or polyurethane-polyorganosiloxane compounds according to the invention can thus be present, for example, in solid or liquid detergent formulations in contents of from about 0.1 to 10 wt. %, based on the total amount of the formulation, and present in cosmetic formulations and fibre treatment formulations, such as textile care compositions, in contents of from about 0.1 to 50 wt. %, based on the total amount of the formulation.

They can furthermore be used for treatment of natural and synthetic fibres, for example cotton, wool and polyester- and polyamide-based synthetic fibres, specifically in the form of textiles, in special compositions for fibre treatment, in particular in detergent formulations containing anionic, nonionic and cationic surfactants, wherein the compounds according to the invention can be incorporated into the detergent directly or metered in separately as the washing process runs or after the washing process, and softness, improved elasticity and reduced tendency to crease are imparted to the substrates treated, while retaining an acceptable hydrophilicity.

They can likewise serve as a constituent of separate softener systems, specifically based on cationic surfactants, after washing of fibres and textiles, as an ironing aid and an agent for preventing or reversing creases in textiles.

They can furthermore be used for finishing fibres, specifically for the first finishing and treatment of, for example, cotton, wool and polyester- and polyamide-based synthetic fibres, specifically in the form of textiles, paper and wood.

As already described above, they can furthermore advantageously be employed in cosmetic systems for treatment of hair and skin.

Particularly preferred fields of use for the polyurea- and polyurethane-polyorganosiloxane compounds according to the invention are also preferably aqueous solutions, mixtures, emulsions and microemulsions, in particular as a base for cosmetic formulations.

The polyurea- and polyurethane-polyorganosiloxane compounds according to the invention can be used as a pure substance, solution, mixture, emulsion or microemulsion in the form of liquids, creams or pastes, as a starting substance for the preparation of suitable cosmetic formulations according to the invention of various viscosities.

The process for the preparation of formulations of the polyurea- and/or polyurethane-polyorganosiloxane compounds according to the invention, such as, for example, for treatment of substrates, such as hard or flexible substrates, can comprise, for example, the following steps:

a) preparation of a premix in the form of solutions, mixtures or emulsions with the polyurea- and/or polyurethane-polyorganosiloxane compounds according to the invention and b) preparation of a further mixture using the premix a) and addition optionally of further surfactants, auxiliary substances and other additives or c) combination of steps a) and b), in which the mixing of the constituents is carried out with stirrers, dissolvers, kneaders, pumps, mixing screws, mixing nozzles, low and high pressure emulsifying apparatuses.

The processes are realized with the machines and apparatuses known in the art (Ullmann's Enzyklopädie), such as e.g. any form of stirrers in suitable containers, apparatuses or mixing equipment, as described above.

Direct mixing of all the constituents is possible. However, the preparation of a premix is preferred, since it leads to faster and better distribution and is partly unavoidable, since the various substance groups otherwise cannot be mixed or emulsified or dispersed with one another in a suitable manner, or can be only with a high outlay. Suitable premixes or intermediate mixtures can preferably be mixtures in the form of solutions, pastes, creams or other forms of emulsions or dispersions. The preparation and use of microemulsions of 10 to 200 nm average particle diameter in cosmetic formulations is particularly preferred.

Alcoholic and polyalcoholic solvents and mixtures thereof with water, oil-like substances and conventional silicones (inter alia polydimethylsiloxanes) and binary and ternary mixtures of solvents and/or oil-like substances and/or silicones are preferably suitable for the preparation of solutions and mixtures which contain the polyurea- and/or polyurethane-polyorganosiloxane compounds according to the invention. Particularly preferred solvents here are ethanol, isopropanol, ethylene glycol and ethylene glycol ethers, polyethylene glycols and ethers thereof, propylene glycol and propylene glycol ethers, polypropylene glycols and ethers thereof and glycerol and mixtures thereof. Particularly preferred oil-like substances are mineral oil products and oils of plant, animal and synthetic origin and mixtures thereof. Particularly preferred silicones, which differ from the polyurea- and/or polyurethane-polyorganosiloxane compounds according to the invention, such as cyclic and linear polydimethylsiloxanes and mixtures thereof, such as e.g. (according to INCI) cyclomethicone, cyclotetrasiloxane, cyclopentasiloxane, cyclohexasiloxane, dimethicone with a viscosity range of from 0.65 to 60,000,000 mPa·s at 25° C. and dimethiconol with a viscosity range of from 10 to 60,000,000 mPas. at 25° C.

Preferred solutions and mixtures which contain the polyurea- and/or polyurethane-polyorganosiloxane compounds according to the invention have the following composition in wt. %, based on the total weight of the composition:

Solutions or Mixtures:

| | |
|---|---|
| 0.1-99.9 wt. % | polyurea- and/or polyurethane-polyorganosiloxane compounds according to the invention |
| 0.1-99.9 wt. % | solvent and/or oil and/or silicones and/or water |

Compositions of emulsions of the polyurea- and/or polyurethane-polyorganosiloxane compounds according to the invention:

For preparation of the emulsions, water and nonionic, cationic and amphoteric surfactants and surfactant mixture are generally used. Emulsions can moreover contain auxiliary substances, such as e.g. inorganic and organic acids, bases and buffers, salts, thickeners, stabilizers for emulsions, such as e.g. "xanthan gum", preservatives, foam stabilizers, defoamers and solvents, such as e.g. alcohols (ethanol, isopropanol, ethylene glycol, polyethylene glycol, propylene glycol, polypropylene glycol, glycol ethers and glycerol and mixtures thereof).

The polyurea- and/or polyurethane-polyorganosiloxane compounds according to the invention which are used in the emulsions can also themselves serve as an emulsifier in the preparation of emulsions.

A preferred emulsion which can preferably be used for the preparation of cosmetic formulations comprises, for example, the following constituents in wt. %, based on the total amount of the composition:

| | |
|---|---|
| 10-50% | polyurea- and/or polyurethane-polyorganosiloxane compounds according to the invention |
| 1-35% | surfactants, |
| 0-10% | auxiliary substances, |
| 0-20% | solvent, |
| to 100% | topped up by water. |

Microemulsions for cosmetic formulations, finishing of textiles and other fibrous substrates or coating of hard surfaces:

The preparation of microemulsions with a high active content of polyurea- and/or polyurethane-polyorganosiloxane compounds according to the invention is particularly preferred, since in addition to the possibility of the preparation of clear cosmetic formulations, these additionally offer the advantage of incorporation into aqueous formulations by simple process technology ("cold process"). There is the possibility of employing the polyurea- and/or polyurethane-polyorganosiloxane compounds according to the invention in the preparation of microemulsions in the form of the solutions and mixtures described above. A preferred active content of the polyurea- and/or polyurethane-polyorganosiloxane compounds according to the invention in the emulsion is between 5 and 60 wt. %, and 10-50 wt. % is particularly preferred, based on the total amount of the composition.

A quite specifically preferred microemulsion comprises the following constituents, which do not, however, limit the invention, in wt. %, based on the total amount of the microemulsion:

| | |
|---|---|
| 20-80% | polyurea- and/or polyurethane-polyorganosiloxane compounds according to the invention |
| 0-35% | surfactants |
| 0-10% | auxiliary substances |
| 0-20% | solvent |
| to 100% | topped up by water. |

The invention also provides the use of the solutions, mixtures or emulsions prepared with the polyurea- and/or polyurethane-polyorganosiloxane compounds according to the invention in a cosmetic formulation.

These cosmetic formulations are prepared using the previously prepared solutions or emulsions, but they can also be produced directly from the individual constituents.

Cosmetic Formulations:

Cosmetic formulations include, for example:

So-called "rinse-off" products, such as e.g. "2-in-1" shampoos, "body wash" and hair rinses for treatment of hair during and after cleansing or after colouring or treatment of hair before bleaching, curling or straightening, and so-called "leave-in" products, such as hair treatments, care creams, hairdressing creams, hair gels, hair styling products, hair setting compositions, hair sprays, pump sprays, blow-waving compositions and blow-drying setting compositions. The formulations moreover likewise include hair colouring compositions, which can be differentiated into 3 types according to the resistance of the colour result achieved to washing—permanent, semipermanent and temporary hair colouring compositions. The term hair here includes all keratin-containing fibres, but in particular human hair. The hair colouring compositions contain, for example, conventional silicones, surfactants, auxiliary substances and colouring agents, in addition to the polyurea- and/or polyurethane-polyorganosiloxane compounds according to the invention. Each of these ingredients can be used either by itself or in combination with further ingredients, and represents additional functions in the formulations which serve to increase the volume, the combability and the shine and to reduce washing out of the colour from and out of coloured keratin-containing substrates, such as e.g. human and animal hair, and contain at least one polyurea- and/or polyurethane-polyorganosiloxane compound.

The abbreviations mentioned in connection with the cosmetic formulations are explained in the INCI (The Cosmetic, Toiletry and Fragrance Association Washington D.C.).

The silicones included here in addition to the polyurea- and/or polyurethane-polyorganosiloxane compounds according to the invention include, for example:

Cyclic, linear and branched polydimethylsiloxanes having a viscosity of 0.65-200,000,000 mPa·s at 25° C. and mixtures thereof, such as e.g. octaorganocyclotetrasiloxanes, octamethylcyclotetrasiloxanes, decaorganocyclopentasiloxanes and dodecaorganocyclohexasiloxanes, wherein the organic radical preferably denotes methyl, such as SF 1173, SF 1202, SF 1217, SF 1204 and SF 1258 from Momentive Performance Materials, dimethicones, such as the Baysilone M oils (M 3 to M 2,000,000), SE 30, SF 1214, SF 1236, SF 1276 and CF 1251 from Momentive Performance Materials, and dimethiconols, such as Baysilone, SiOH-terminated polyorganosiloxane gums from Momentive Performance Materials and DC 1501 and DC 1503 from Dow Corning.

The use of the polydimethylsiloxanes described above in the form of nonionic, anionic and cationic emulsions, such as e.g. SM 2169, SM 2785, SM 555, SM 2167 and SM 2112 from Momentive Performance Materials in combination with emulsions of the polyurea- and/or polyurethane-polyorganosiloxane compounds according to the invention and/or the use of mixtures and solutions of the polydimethylsiloxanes described above with the polyurea- and/or polyurethane-polyorganosiloxane compounds according to the invention is particularly preferred here, since particular properties of hair care products can be derived from these combinations, such as has already been described extensively in the literature for amino-functional silicones known to date (WO 99/44565, WO 99/44567, WO 99/49836, WO 99/53889, WO 97/12594, U.S. Pat. No. 6,028,031, EP 0811371, WO 98/18443, WO 98/43599 and US 2002-0182161).

Solid silicones, so-called MQ resins, such as e.g. SR 1000 from Momentive Performance Materials, and solutions thereof in solvents, such as the abovementioned silicones and aliphatic solvents, such as e.g. isododecane, are likewise suitable.

Organofunctional silicones, such as alkyl-, aryl-, arylalkyl-, phenyl-, fluoroalkyl- and polyether-modified silicones, such as the types SF 1632, SF 1642, SF 1555, Baysilone CF 1301, Baysilone PK 20, FF 157, SF 1188A, SF 1288 and SF 1388 from Momentive Performance Materials, are likewise suitable.

Surfactants:

Surfactants as ingredients of cosmetic formulations are described in A. Domsch: Die kosmetischen Präparate, Verlag für Chem. Industrie, 4th edition, 1992, in Kosmetikjahrbuch 1995, Verlag für chemische Industrie, 1995, and H. Stache, Tensidtaschenbuch, 2nd edition, Carl Hanser Verlag, 1981.

Anionic Surfactants:

By way of example but without being limited thereto, the following anionic surfactants are suitable as a constituent of the formulations:

alkyl sulfates, alkyl ether-sulfates, alkaryl sulfates, olefinsulfonates, alkylamide ether-sulfates, acyl isethionates, acyl glutamates, alkyl ether-carboxylates, methyl taurides and taurides, sarcosides, sulfosuccinates, protein-fatty acid condensates, alkyl phosphates and alkyl ether-phosphates. The free acids and alkali metal salts, magnesium, ammonium and mono-, di- and triethanolamine salts thereof can be used here.

The alkyl and acyl groups typically contain 8-18 C atoms and can be unsaturated. The alkyl ether-sulfates, alkylamide ether-sulfates, alkyl ether-carboxylates and alkyl ether-phosphates can contain 1-10 ethylene oxide or propylene oxide units or a combination of ethylene oxide and propylene oxide units.

Amphoteric Surfactants:

By way of example but without being limited thereto, the following amphoteric surfactants are suitable as a constituent of the formulations:

Alkylbetaines, alkyl amidobetaines, sulfobetaines, acetates and diacetates, imidazolines, propionates and alkylamine oxides.

The alkyl and acyl groups here contain 8-19 C atoms.

Nonionic Surfactants:

By way of example but without being limited thereto, the following nonionic surfactants are suitable as a constituent of the formulations:

Alkyl ethoxylates, aryl ethoxylates, ethoxylated esters, polyglycolamides, polysorbates, glycerol fatty acid ethoxylates, alkylphenol polyglycol ethers and sugar surfactants, such as e.g. alkyl glycosides.

Cationic Surfactants:

In the case of cationic surfactants, a distinction is made between pure cationic surfactants and cationic polymers.

Pure Cationic Surfactants:

By way of example but without being limited thereto, the following cationic surfactants are suitable as a constituent of the formulations:

Monoalkylquats, dialkylquats, trialkylquats, tetraalkylquats, benzylammonium salts, pyridine salts, alkanolammonium salts, imidazoline salts, oxazoline salts, thiazoline salts, salts of amine oxides and sulfone salts, wherein the term "quat" implies the presence at least of one quaternary ammonium group.

Cationic Polymers:

For "2-in-1" shampoos in particular, cationically modified polymers are also employed, in addition to the pure cationic surfactants. A comprehensive description of these polymers is given in U.S. Pat. No. 5,977,038 and WO 01/41720 A1. Cationic polyacrylamides, cationic protein derivatives, hydroxyalkylcellulose ethers and cationic guar derivatives are preferred here. Cationic guar derivatives with the CTFA name Guar Hydroxypropyltrimonium Chloride are particularly preferred. These types are obtainable under the trade names Cosmedia Guar C 261 (Henkel), Diagum P 5070 (Diamalt) and Jaguar C types and Jaguar EXCEL from Rhodia.

Auxiliary Substances:

Auxiliary substances as ingredients in particular of cosmetic formulations are described in: A. Domsch, Die kosmetischen Präparate, Verlag für chem. Industrie, 4th edition, 1992; and in: Kosmetikjahrbuch 1995, Verlag für chemische Industrie, 1995.

By way of example but without being limited thereto, the following auxiliary substances are suitable as a constituent of the formulations:

Inorganic and organic acids, bases and buffers, salts, alcohols, such as e.g. ethanol, isopropanol, ethylene glycol, polyethylene glycol, propylene glycol, polypropylene glycol, glycol ethers and glycerol, thickeners, stabilizers for emulsions, such as e.g. xanthan gum, re-oiling agents, preservatives, foam stabilizers, defoamers, pearlescent and opacifying agents, such as e.g. glycol distearates and titanium dioxide, collagen hydrolysate, keratin hydrolysate, silk hydrolysate, antidandruff active compounds, such as e.g. zinc pyrithione, salicylic acid, selenium disulfide, sulfur and tar preparations, polymeric emulsifiers, vitamins, dyestuffs, substances for filtering UV rays, bentonites, perfume oils, fragrances, styling polymers, moisturizers, plant extracts and further natural or nature-identical raw materials.

It is known that by the addition of oil- and water-soluble UV filters or combinations of UV filters in cosmetic formulations for care and treatment of keratin-containing substrates, such as human and animal hair, the degradation of dyestuffs and therefore the bleaching out and fading of coloured keratin-containing substrates by UV radiation can be reduced decisively or even prevented completely.

Ingredients for Hair Colouring Compositions:

Dyestuffs and other ingredients of hair colouring compositions are described in: A. Domsch, Die kosmetischen Präparate, Verlag für chem. Industrie, 4th edition, 1992. Dyestuffs are described in: Legislation on cosmetic agents (Cosmetics Legislation), Bundesgesetzblatt 1997, part I p. 2412, §3 and annex 3 and in European Community (EC) Directive, 76/68/EEC, annex IV.

In the following, hair colouring compositions are differentiated into permanent, semipermanent and temporary hair colour compositions.

Permanent Hair Colouring Compositions:

Permanent dyeings which are not washed out even by washing the hair several times (more than 10) are formed by chemical reaction between dyestuff precursors under oxidative conditions by hydrogen peroxide. The mixture of the corresponding components determines the colour result which can be achieved here.

In the case of the precursors, a distinction is made between oxidation bases (developers) and coupling components (modifiers).

Oxidation Bases:

By way of example but without being limited thereto, the following oxidation bases are suitable as a constituent of the formulations:

m- and p-phenylenediamines (diaminobenzenes), N-substituted derivatives and salts thereof, N-substituted derivatives of o-phenylenediamine, o-, m- and p-toluylenediamines (methyl-diaminobenzenes), N-substituted derivatives and salts thereof, p-amino-diphenylamine and its hydrochloride and sulfate, o-, m- and p-aminophenol and its hydrochloride, 2,4-diaminoisosulfate (4-methoxy-m-phenylenediamine sulfate), o-chloro-p-phenylenediamine sulfate, picramic acid (2,4-dinitro-6-aminophenol) and 2,4-dinitro-1-naphtholsulfonic acid and the sodium salt thereof.

Coupling Components:

By way of example but without being limited thereto, the following coupling components are suitable as a constituent of the formulations:

Hydroquinone (1,4-dihydroxybenzene), resorcinol (1,3-dihydroxybenzene), pyrocatechol (1,2-dihydroxybenzene), α-naphthol (1-hydroxynaphthalene), pyrogallol (1,2,3-trihydroxybenzene) and 2,6-diaminopyridine.

Oxidation bases and coupling components are conventionally incorporated with surfactants into oil-in-water emulsions, but simple solutions or shampoos are also known as formulations. The formulations moreover contain antioxidants, such as e.g. sodium sulfite, sodium dithionite, ascorbic acid or thioglycollic acid, to stabilize the precursors and are adjusted to a pH of between 8 and 12 (preferably 9-11) with alkaline substances, such as e.g. ammonia. Surfactants as wetting agents, complexing agents for heavy metals, fragrances for masking the ammonia smell, conditioners for improving the feel of the hair and for protecting the hair and solvents, such as ethanol, ethylene glycol, glycerol or benzyl alcohol, are moreover added.

Permanent hair colouring compositions are typically on offer as 2-component systems comprising the colour solution, cream or shampoo described above and the developer solution. The developer solution here contains between 6-12 wt. % of hydrogen peroxide, and constituents of the formulation containing the colour components can optionally also be added. The peroxide solution here, however, must be thoroughly stabilized.

Semipermanent Hair Colouring Compositions:

Semipermanent colourings were developed to maintain the colouring for 6-10 washes with shampoo. So-called directly-absorbing dyestuffs which essentially belong to the group of nitro, azo and anthraquinone dyestuffs are used here. These dyestuff molecules are small enough to penetrate into the hair. Formulations which are typically employed are solutions, creams, shampoos or also aerosol foams. The composition is comparable to the formulations containing the colour component which are as permanent hair colourings.

Temporary Hair Colouring Compositions:

In contrast to the semipermanent hair colouring compositions, temporary colourings, also called tints, contain larger dyestuff molecules which are not capable of penetrating into the hair. They were developed to maintain the colouring for 1-6 washes. Azo and basic dyestuffs and azine and thiazine derivatives are typically employed here. That stated for the semipermanent and permanent hair colouring compositions applies to the composition of the formulations. Dyestuffs and other ingredients of hair colouring compositions are described in: A. Domsch, Die kosmetischen Präparate, Verlag für chem. Industrie, 4th edition, 1992. Dyestuffs are described in: Legislation on cosmetic agents (Cosmetics Legislation), Bundesgesetzblatt 1997, part I p. 2412, §3 and annex 3 and in European Community (EC) Directive, 76/68/EEC, annex IV.

The following recipes, which do not, however, limit the invention, in which each functional active compound can occur as an individual compound or as a mixture of several compounds of this category, have been found to be particularly advantageous for the use of mixtures containing the polyurea- and/or polyurethane-polyorganosiloxane compounds according to the invention in cosmetic formulations.

A typical shampoo formulation according to the invention, which does not, however, limit the invention, for care and conditioning of hair comprises the following constituents in wt. %, in each case based on the total formulation:

| | |
|---|---|
| 0.01-10% | polyurea- and/or polyurethane-polyorganosiloxane compounds according to the invention |
| 2-15% | anionic surfactant |
| 0-10% | amphoteric surfactant |
| 0-15% | nonionic surfactant |
| 0-10% | cationic surfactant |
| 0-10% | silicone conditioning agents (co-adjuvants) |
| 0-10% | auxiliary substances |
| to 100% | topped up by water. |

A specific shampoo formulation, which does not, however, limit the invention, comprises the following constituents in wt. %:

| | |
|---|---|
| 0.1-12% | polyurea- and/or polyurethane-polyorganosiloxane compounds according to the invention |
| 1-35% | sodium or ammonium lauryl or laureth sulfate (20-30%) |
| 1-6% | cocoamidopropylbetaine (25-35%) |
| 0-3% | guar hydroxypropyltrimonium chloride |
| 0-5% | polyquaternium-10 |
| 0-12% | silicone conditioning agents (co-adjuvants) |
| 0.01-1% | disodium EDTA |
| 0.01-1% | phenoxyethanol (and) methylparaben (and) butylparaben (and) ethylparaben (and) propylparaben |
| 0-1% | perfume (fragrance) |
| 0-1% | dyestuffs |
| 0-1% | citric acid |
| 0-2% | sodium chloride |
| to 100% | topped up by water. |

A typical hair rinse according to the invention, which does not, however, limit the invention, for care and conditioning of hair comprises the following constituents in wt. %:

| | |
|---|---|
| 0.1-15% | polyurea- and/or polyurethane-polyorganosiloxane compounds according to the invention |
| 0-10% | amphoteric surfactant |
| 0.1-15% | nonionic surfactant |
| 0-10% | cationic surfactant |
| 0-15% | silicone conditioning agents (co-adjuvants) |
| 0-20% | auxiliary substances |
| to 100% | topped up by water. |

A specific composition of a hair rinse, which does not, however, limit the invention, comprises the following constituents in wt. %:

| | |
|---|---|
| 0.5-15% | polyurea- and/or polyurethane-polyorganosiloxane compounds according to the invention (as a 43.5% strength emulsion in water with nonionic emulsifiers) |
| 0-15% | silicone conditioning agents (co-adjuvants) |
| 0-10% | cetrimonium chloride (25-35%) |
| 0-3% | guar hydroxypropyltrimonium chloride |
| 1-10% | cetearyl alcohol |
| 0-10% | glycerol |
| 0.01-1% | phenoxyethanol (and) methylparaben (and) butylparaben (and) ethylparaben (and) propylparaben |

A typical hair care treatment according to the invention for care and conditioning of hair comprises the following constituents in wt. %:

| | |
|---|---|
| 0.4-20% | polyurea- and/or polyurethane-polyorganosiloxane compounds according to the invention |
| 0-15% | nonionic surfactant |
| 0-10% | cationic surfactant |
| 0-20% | silicone conditioning agents (co-adjuvants) |
| 0-20% | auxiliary substances |
| to 100% | topped up by water. |

A specific hair care treatment comprises the following constituents in wt. %:

| | |
|---|---|
| 1-20% | polyurea- and/or polyurethane-polyorganosiloxane compounds according to the invention (as a 43.5% strength emulsion in water with nonionic emulsifiers) |
| 0.5-10% | stearyl alcohol (and) steareth-7 (and) steareth-10 |
| 0-20% | silicone conditioning agents (co-adjuvants) |
| 0-10% | cetrimonium chloride (25-35%) |
| 0-3% | guar hydroxypropyltrimonium chloride |
| 0-5% | dimethicone |
| 0-5% | paraffin oil |
| 1-10% | stearyl alcohol |
| 0-10% | glycerol |
| 0.01-1% | phenoxyethanol (and) methylparaben (and) butylparaben (and) ethylparaben (and) propylparaben |
| 0-1% | perfume (fragrance) |
| 0-1% | dyestuffs |
| 0-1% | citric acid |
| 0-2% | sodium chloride |
| to 100% | topped up by water. |

A quite specific hair care treatment comprises the following constituents in wt. %:

| | |
|---|---|
| 2-5% | polyurea- and/or polyurethane-polyorganosiloxane compounds according to the invention (as a 43.5% strength emulsion in water with nonionic emulsifiers) |
| 0-5% | silicone conditioning agents (co-adjuvants) |
| 0-2% | cetrimonium chloride (25-35%) |
| 0.5-5% | glycerol |
| 0.25-2.5% | propylene glycol |
| 0.05-0.2% | Perfume |
| 0.1-0.5% | polysorbate 20 |
| to 100% | topped up by water. |

A typical dyestuffs-containing formulation according to the invention, which does not, however, limit the invention, for temporary, semipermanent or permanent hair colouring, care and conditioning of hair comprises the following constituents in wt. %:

| | |
|---|---|
| 0.1-10% | polyurea- and/or polyurethane-polyorganosiloxane compounds according to the invention |
| 1-10% | hair dyestuff precursors or dyestuffs according to the desired hair colour |
| 0-15% | anionic surfactant |
| 0-10% | amphoteric surfactant |
| 0-10% | nonionic surfactant |
| 0-10% | cationic surfactant |
| 0-1% | sodium sulfite |
| 0-5% | buffer |
| 0-10% | silicone conditioning agents (co-adjuvants) |
| 0-10% | auxiliary substances |
| to 100% | water. |

A specific colour cream for permanent hair colouring comprises the following constituents in wt. %:

| | |
|---|---|
| 0.1-10% | polyurea- and/or polyurethane-polyorganosiloxane compounds according to the invention (as a 20% strength emulsion in water with nonionic emulsifiers) |
| 1-5% | hair colour precursors or dyestuffs according to the desired hair colour |
| 2-15% | anionic surfactant |
| 0-10% | amphoteric surfactant |
| 0-10% | nonionic surfactant |
| 0-10% | cationic surfactant |
| 0.1-1% | sodium sulfite |
| 0.1-5% | buffer for pH = 8-12 |
| 0-10% | silicone conditioning agents (co-adjuvants) |
| 0-10% | auxiliary substances |
| to 100% | water. |

A specific colour solution according to the invention, which does not, however, limit the invention, for permanent hair colouring comprises the following constituents in wt. %:

| | |
|---|---|
| 0.1-10% | polyurea- and/or polyurethane-polyorganosiloxane compounds according to the invention (as a 20% strength emulsion in water with nonionic emulsifiers) |
| 1-5% | hair colour precursors or dyestuffs according to the desired hair colour |
| 0.1-1% | sodium sulfite |
| 5-15% | propylene glycol |
| 5-15% | ammonia (28%). |
| 10-30% | oleic acid |
| 5-15% | isopropanol |
| 10-30% | alkanolamide |
| 0-10% | silicone conditioning agents (co-adjuvants) |
| to 100% | water. |

A typical developer formulation according to the invention, which does not, however, limit the invention, for permanent hair colouring comprises the following constituents in wt. %:

| | |
|---|---|
| 0.1-10% | polyurea- and/or polyurethane-polyorganosiloxane compounds according to the invention |
| 10-30% | hydrogen peroxide (30%) |
| 0-15% | anionic surfactant |
| 0-10% | amphoteric surfactant |
| 0-10% | nonionic surfactant |
| 0-10% | cationic surfactant |
| 0-5% | buffer or acid for pH = 2-6 |
| 0-10% | silicone conditioning agents (co-adjuvants) |
| 0-10% | auxiliary substances |
| to 100% | water |

A specific developer cream according to the invention, which does not, however, limit the invention, for permanent hair colouring comprises the following constituents in wt. %:

| | |
|---|---|
| 0.1-5% | polyurea- and/or polyurethane-polyorganosiloxane compounds according to the invention (as a 20% strength emulsion in water with nonionic emulsifiers) |

| | |
|---|---|
| 10-30% | hydrogen peroxide (30%) |
| 0-5% | silicone conditioning agents (co-adjuvants) |
| 1-10% | cetearyl alcohol |
| 0.5-5% | trideceth-2 carboxamide MEA |
| 0.5-5% | ceteareth-30 |
| 0.5-5% | glycerol |
| 0.05-2% | pentasodium pentetate (pentasodium diethylene-triaminepentaacetate |
| 0.05-2% | sodium stannate |
| 0.05-2% | tetrasodium pyrophosphate |
| to 100% | water. |

It has been found here that the solutions or mixtures according to the invention are preferably suitable for the preparation of cosmetic formulations, such as for the treatment, conditioning, cleansing and/or care of coloured substrates or substrates which are to be coloured.

That is to say the formulations containing at least one polyurea- and/or polyurethane-polyorganosiloxane compound according to the invention can be employed in particular for cleansing, care and conditioning of fibrous or planar substrates, and if these are coloured and the colour impression thereof is to be largely retained.

The formulations containing at least one polyurea- and/or polyurethane-polyorganosiloxane compound according to the invention can furthermore serve for the cleansing, care and the treatment and the conditioning of keratin-containing substrates, since they are suitable as cleansing compositions for wool, for washing and/or increasing the volume and/or the combability and/or the shine and/or for reducing the washing out of colour from and out of keratin-containing substrates which are coloured or from keratin-containing substrates which are simultaneously to be coloured, such as e.g. human and animal hair.

The formulations containing at least one polyurea- and/or polyurethane-polyorganosiloxane compound according to the invention can furthermore be used in particular for the cleansing, the treatment and care, cleansing and care of keratin-containing fibres or hair before, during and/or after the colouring operation, since the hair colouring compositions formulated with these lead simultaneously to an improvement in the softness and/or to a reduction in the wet and dry combing forces and/or to an increase in the shine and/or to an increase in the hair volume and/or to a reduction in the washing out of dyestuffs from and out of tinted and coloured hair.

Fabric Softener Formulations

With respect to the presentation form, on the one hand it is possible to incorporate the polyurea- and/or polyurethane-polyorganosiloxane compounds according to the invention into non-transparent fabric softener dispersions or fabric softener emulsions or transparent microemulsions or solutions.

Typical further components for such non-transparent or transparent formulations are:
- quaternary ammonium compounds, preferably quaternary ammonium compounds containing alkanoic acid ester units, as softeners,
- organic solvents, preferably mono- and polyhydric alcohols, such as ethanol, 2-propanol, ethylene glycol, 1,2-propylene glycol, hexylene glycol, dipropylene glycol, esters and ethers of glycols and oligoglycols, such as dipropylene glycol monobutyl ether, tripropylene glycol monomethyl ether, diethylene glycol diacetate, to improve the solubility and transparency of the formulation,
- diols and higher alcohols of longer-chain hydrocarbons, for example 2,2,4-trimethyl-1,3-pentanediol, for increasing the solubilizability of the softener components,
- nonionic surfactants, preferably alkoxylates of branched or unbranched $C_8$ to $C_{40}$-alcohols and fatty acid esters of alkylene oxides for stabilization of the emulsion or preparation of a microemulsion
- perfumes
- viscosity regulators
- dyestuffs
- preservatives.

The additional functional components listed and preferred representatives are known, for example, from U.S. Pat. No. 6,376,455.

It is furthermore possible to apply the polyurea- and/or polyurethane-polyorganosiloxane compound according to the invention to solid carriers in the context of laundry freshener systems, and then to bring these into contact, in the laundry dryer, with textiles which are to be freshened and/or softened. Laundry freshener systems on carriers and functional components thereof are known, for example, from U.S. Pat. No. 4,824,582, U.S. Pat. No. 4,808,086, U.S. Pat. No. 4,756,850, U.S. Pat. No. 4,749,596 and U.S. Pat. No. 3,686,025.

Typical components for such laundry freshener systems on carriers are:
- fatty amines or complexes thereof with anionic surfactants as conditioning agents
- quaternary ammonium compounds, preferably quaternary ammonium compounds containing alkanoic acid ester units, as softeners,
- nonionic softeners, for example based on sorbitan esters, fatty alcohol alkoxylates
- "soil release agents", for example based on cellulose ethers, guar gum, terephthalic acid block copolymers.

The carrier material is a sponge-like or porous sheet-like material which has a sufficient capacity for uptake of the laundry freshener formulation. "Woven" and "nonwoven" materials are employed. The materials are based on natural or synthetic polymers, such as wool, cotton, sisal, linen, cellulose esters, polyvinyl compounds, polyolefins, polyamides, polyurethanes and polyesters.

The present invention is illustrated further by the following examples.

EXAMPLES

Example 1

58 g of Methoxypropyl Acetate, 7.19 g (10.8 mmol) of an Isocyanate-Terminated Polyalkylene Oxide Derivative of the Structure

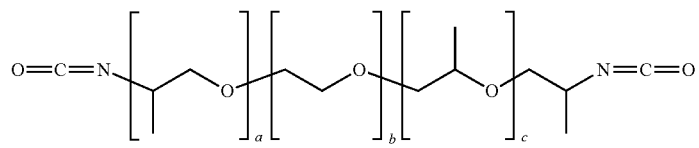

where a+c=3.6 and b=9
and 50 g of an aminosiloxane of the structure

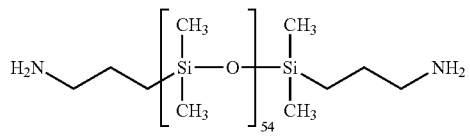

are mixed in a flask at room temperature under an $N_2$ atmosphere. The temperature rises to 30° C. The mixture is heated at 95 to 100° C. for 10 hours.

As a result of the reaction, a clear yellow solution is obtained, which contains a polymer with the following structural element:

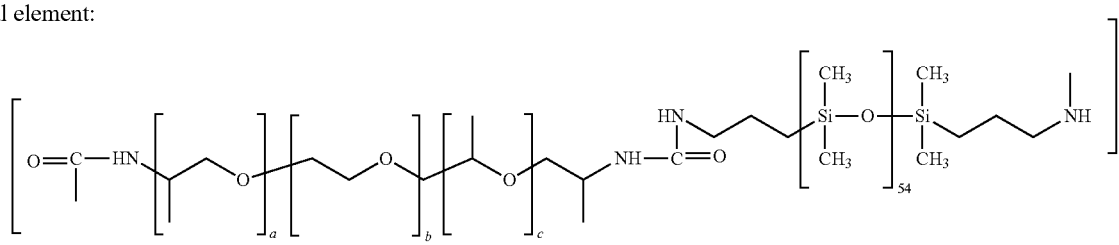

where a+c=3.6 and b=9

Example 2

58 g of Methoxypropyl Acetate, 5.34 g (8.04 mmol) of an Isocyanate-Terminated Polyalkylene Oxide Derivative of the Structure

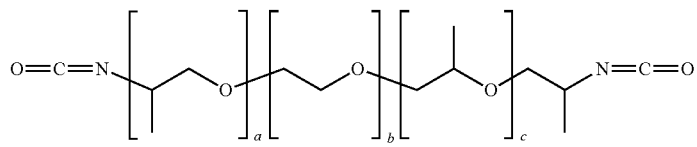

where a+c=3.6 and b=9 and 1.69 g (16.1 mmol) of $H_2NCH_2CH_2CH_2N(CH_3)_2$ are initially introduced into a flask at room temperature under an $N_2$ atmosphere and the mixture is heated at 95-100° C. for 6 hours, while stirring.

A mixture comprising 50 g (8.04 mmol) of an epoxysiloxane of the structure

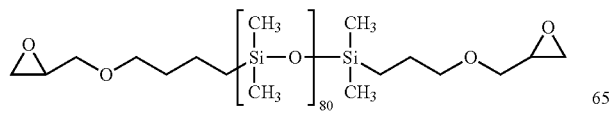

1 g of deionized water and 0.97 g (16.1 mmol) of acetic acid is then added. The total mixture is heated at 95-100° C. for 10 hours.

As a result of the reaction, a reddish, cloudy solution is obtained, which contains a polymer with the following structural element:

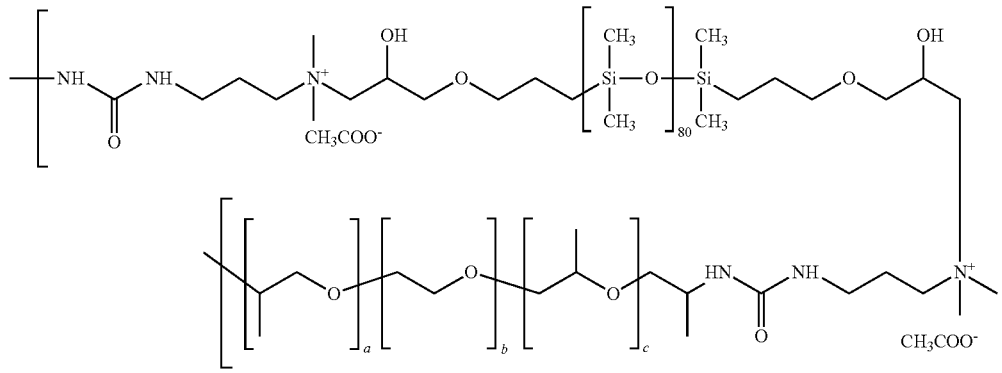

where a+c=3.6 and b=9

The polymers according to Examples 1 and 2 can be incorporated in an amount of, for example, 0.5-3% into pulverulent and liquid detergents based on anionic and/or nonionic surfactants, and exert there in particular, with a high substantivity, their softening action on the fibre materials to be cleaned.

The invention claimed is:

1. Polyurea-polysiloxane compounds consisting of at least one structural element of the formula (1):

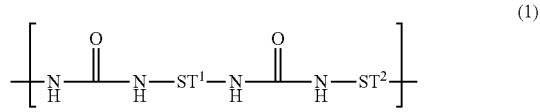

wherein

ST$^1$ is chosen from divalent or higher valency, straight-chain, cyclic or branched, saturated, unsaturated or aromatic, substituted or unsubstituted hydrocarbon radicals having up to 1,000 carbon atoms exclusive of the carbon atoms of an optional polyorganosiloxane unit, which can contain one or more groups chosen from —O—, —C(O)—, —NH—, —NR$^3$—,

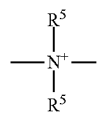

and a polydiorganosiloxane unit having 2 to 1,000 silicon atoms, wherein R$^3$ is a straight-chain, cyclic or branched, saturated, unsaturated or aromatic hydrocarbon radical having up to 40 carbon atoms, which can contain one or more groups chosen from —O—, —C(O)— and —NH—, and R$^5$ is a straight-chain, cyclic or branched, saturated, unsaturated or aromatic hydrocarbon radical having up to 100 carbon atoms, which can contain one or more groups chosen from —O—, —C(O)— and —NH—, or R$^5$ is a divalent radical which forms cyclic structures within the radicals ST$^1$ and/or ST$^2$, and ST$^2$ is a radical of the formula (2)

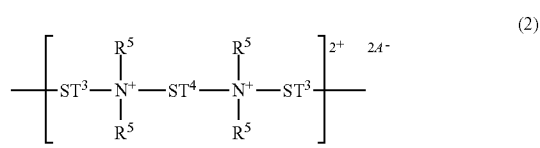

wherein

ST$^3$ is a straight-chain or cyclic or branched, saturated or unsaturated or aromatic, substituted or unsubstituted hydrocarbon radical having 2 to 100 carbon atoms, which can be substituted by —O—, —C(O)—, —NH—, —NR$^3$—, wherein R$^3$ is as defined above, ST$^4$ is a straight-chain or cyclic or branched, saturated or unsaturated or aromatic, substituted or unsubstituted hydrocarbon radical having 2 to 100 carbon atoms exclusive of the carbon atoms of an optional polyorganosiloxane unit, which can be substituted by —O—, —C(O)—, —NH—, —NR$^3$— and by a polydiorganosiloxane unit having 2 to 200 silicon atoms, wherein R$^3$ is as defined above, and A$^-$ is an organic or inorganic anion, with the proviso that at least one of the radicals ST$^1$, ST$^4$ contains a polydiorganosiloxane radical, or acid addition compounds and/or salts of the foregoing.

2. The polyurea-polysiloxane compounds of claim 1, containing at least one polydiorganosiloxane structural element of the formula (6):

wherein

R$^4$ is a straight-chain, cyclic or branched, saturated, unsaturated or aromatic, substituted or unsubstituted hydrocarbon radical having up to 20 C atoms, and s=1 to 999.

3. The polyurea-polysiloxane compounds of claim 2, wherein $R^4$ is a $C_1$ to $C_{20}$ straight-chain or cyclic or branched, saturated or unsaturated or aromatic hydrocarbon radical, and s is 1 to 199.

4. The polyurea-polysiloxane compounds of claim 3, containing at least one polydiorganosiloxane structural element of the formula (6')

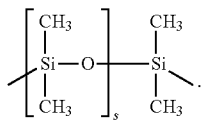 (6')

5. The polyurea-polysiloxane compounds of claim 1, containing at least two structural elements of the formula (1).

6. The polyurea-polysiloxane compounds of claim 4, containing on average at least two structural elements of the formula (6) or (6').

7. The polyurea-polysiloxane compounds of claim 1, wherein the radicals $ST^1$, $ST^2$, $ST^3$ and $ST^4$ are divalent radicals, so that the polyurea-polyorganosiloxane compounds are linear in structure.

8. The polyurea-polysiloxane compounds of claim 2, containing at least one radical of the formula:

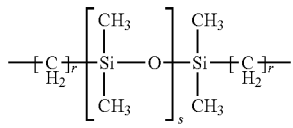

wherein r is from 1 to 12.

9. The polyurea-polysiloxane compounds of claim 1, containing at least one polyalkylene oxide radical.

* * * * *